(12) United States Patent
Hughes et al.

(10) Patent No.: US 8,377,027 B2
(45) Date of Patent: Feb. 19, 2013

(54) WAIST ELASTIC MEMBERS FOR USE IN ABSORBENT ARTICLES

(75) Inventors: Janis W. Hughes, Alpharetta, GA (US); Varunesh Sharma, Atlanta, GA (US); Prasad Shrikrishna Potnis, Duluth, GA (US); Gregory Hall, Menasha, WI (US); Thomas H. Roessler, Appleton, WI (US); Peiguang Zhou, Appleton, WI (US); Stephen C. Baumgartner, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1172 days.

(21) Appl. No.: 11/118,603

(22) Filed: Apr. 29, 2005

(65) Prior Publication Data

US 2006/0247591 A1    Nov. 2, 2006

(51) Int. Cl.
*A61F 13/15* (2006.01)
*A61F 13/20* (2006.01)

(52) U.S. Cl. ........... 604/385.3; 604/383; 604/385.24; 604/385.01

(58) Field of Classification Search .......... 604/373, 604/383, 385.01, 385.22, 385.24–385.3, 604/392–96
See application file for complete search history.

(56) References Cited

U.S. PATENT DOCUMENTS

| | | | |
|---|---|---|---|
| 2,544,069 A * | 3/1951 | Cutler | 2/400 |
| 3,338,992 A | 8/1967 | Kinney | |
| 3,341,394 A | 9/1967 | Kinney | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,855,046 A | 12/1974 | Hansen et al. | |
| 4,041,203 A | 8/1977 | Brock et al. | |
| 4,100,324 A | 7/1978 | Anderson et al. | |
| 4,166,464 A * | 9/1979 | Korpman | 604/366 |
| 4,300,562 A * | 11/1981 | Pieniak | 604/385.26 |
| 4,333,782 A * | 6/1982 | Pieniak | 156/164 |
| 4,340,563 A | 7/1982 | Appel et al. | |
| 4,374,888 A | 2/1983 | Bornslaeger | |
| 4,395,215 A * | 7/1983 | Bishop | 425/290 |

(Continued)

FOREIGN PATENT DOCUMENTS

| | | |
|---|---|---|
| EP | 0217032 B1 | 4/1987 |
| EP | 0634453 A2 | 1/1995 |

(Continued)

OTHER PUBLICATIONS

Definition of "proximal", Merriam-Webster OnLine.*

(Continued)

*Primary Examiner* — Susan Su
(74) *Attorney, Agent, or Firm* — Dority & Manning, P.A.

(57) ABSTRACT

Absorbent articles having form fitting properties are disclosed. In particular, the absorbent articles include at least one waist elastic member that extends a substantial distance in the longitudinal direction. The waist elastic member, for instance, may be positioned in a front region of the article, in a back region of the article or in both the front and back regions. The waist elastic member includes a breathable elastic film. In order for the film to be breathable, the film includes apertures. The apertures appear on the film according to a particular pattern and having a particular diameter so that the film retains desired stretch properties.

20 Claims, 6 Drawing Sheets

U.S. PATENT DOCUMENTS

| | | | | |
|---|---|---|---|---|
| 4,450,026 | A | * | 5/1984 | Pieniak et al. ............... 156/164 |
| 4,573,991 | A | * | 3/1986 | Pieniak et al. ........... 604/385.26 |
| 4,641,381 | A | | 2/1987 | Heran et al. |
| 4,652,487 | A | | 3/1987 | Morman |
| 4,655,760 | A | | 4/1987 | Morman et al. |
| 4,657,802 | A | | 4/1987 | Morman |
| 4,663,220 | A | | 5/1987 | Wisneski et al. |
| 4,704,116 | A | | 11/1987 | Enloe |
| 4,710,189 | A | * | 12/1987 | Lash ....................... 604/385.27 |
| 4,720,415 | A | | 1/1988 | Vander Wielen et al. |
| 4,731,066 | A | * | 3/1988 | Korpman ..................... 604/366 |
| 4,747,991 | A | * | 5/1988 | Bishop ......................... 264/504 |
| 4,781,966 | A | | 11/1988 | Taylor |
| 4,789,699 | A | | 12/1988 | Kieffer et al. |
| 4,795,668 | A | | 1/1989 | Krueger et al. |
| 4,798,603 | A | | 1/1989 | Meyer et al. |
| 4,798,604 | A | * | 1/1989 | Carter ........................... 604/383 |
| 4,818,464 | A | | 4/1989 | Lau |
| 4,834,738 | A | * | 5/1989 | Kielpikowski et al. .. 604/385.22 |
| 4,842,596 | A | | 6/1989 | Kielpikowski et al. |
| 4,940,464 | A | | 7/1990 | Van Gompel et al. |
| 4,965,122 | A | | 10/1990 | Morman |
| 4,981,747 | A | | 1/1991 | Morman |
| 5,057,368 | A | | 10/1991 | Largman et al. |
| 5,069,970 | A | | 12/1991 | Largman et al. |
| 5,108,820 | A | | 4/1992 | Kaneko et al. |
| 5,145,727 | A | | 9/1992 | Potts et al. |
| 5,151,092 | A | * | 9/1992 | Buell et al. ................. 604/385.3 |
| 5,169,706 | A | | 12/1992 | Collier, IV et al. |
| 5,176,668 | A | | 1/1993 | Bernardin |
| 5,176,672 | A | | 1/1993 | Bruemmer et al. |
| 5,178,931 | A | | 1/1993 | Perkins et al. |
| 5,188,885 | A | | 2/1993 | Timmons et al. |
| 5,192,606 | A | | 3/1993 | Proxmire et al. |
| 5,284,703 | A | | 2/1994 | Everhart et al. |
| 5,336,545 | A | | 8/1994 | Morman |
| 5,336,552 | A | | 8/1994 | Strack et al. |
| 5,350,624 | A | | 9/1994 | Georger et al. |
| 5,376,198 | A | * | 12/1994 | Fahrenkrug et al. .......... 156/164 |
| 5,382,400 | A | | 1/1995 | Pike et al. |
| 5,385,775 | A | | 1/1995 | Wright |
| 5,399,219 | A | | 3/1995 | Roessler et al. |
| 5,466,410 | A | | 11/1995 | Hills |
| 5,486,166 | A | | 1/1996 | Bishop et al. |
| 5,490,846 | A | | 2/1996 | Ellis et al. |
| 5,509,915 | A | | 4/1996 | Hanson et al. |
| 5,514,470 | A | | 5/1996 | Haffner et al. |
| 5,540,796 | A | | 7/1996 | Fries |
| H1583 | H | | 8/1996 | Hwo et al. |
| 5,567,501 | A | * | 10/1996 | Srinivasan et al. ............. 428/137 |
| 5,595,618 | A | | 1/1997 | Fries et al. |
| 5,601,547 | A | | 2/1997 | Kato et al. |
| 5,628,097 | A | * | 5/1997 | Benson et al. ................... 28/165 |
| 5,669,897 | A | * | 9/1997 | Lavon et al. ................ 604/385.24 |
| 5,685,874 | A | * | 11/1997 | Buell et al. ..................... 604/396 |
| 5,766,389 | A | | 6/1998 | Brandon et al. |
| 5,804,021 | A | * | 9/1998 | Abuto et al. .................... 156/252 |
| 5,820,973 | A | | 10/1998 | Dodge, II et al. |
| 5,851,935 | A | * | 12/1998 | Srinivasan et al. ............. 442/328 |
| 6,004,306 | A | * | 12/1999 | Robles et al. ............. 604/385.21 |
| 6,022,612 | A | | 2/2000 | Wilkie |
| 6,025,071 | A | | 2/2000 | Cameron et al. |
| 6,090,234 | A | * | 7/2000 | Barone et al. ................... 156/177 |
| 6,093,663 | A | * | 7/2000 | Ouellette et al. ................... 442/5 |
| 6,162,859 | A | | 12/2000 | Lu et al. |
| 6,184,285 | B1 | | 2/2001 | Hatfield et al. |
| 6,226,992 | B1 | | 5/2001 | Kutlucinar et al. |
| 6,277,976 | B1 | | 8/2001 | Enmark et al. |
| 6,340,782 | B1 | * | 1/2002 | Kling et al. ..................... 604/366 |
| 6,384,138 | B1 | | 5/2002 | Jacob et al. |
| H2036 | H | | 7/2002 | Bush |
| 6,452,063 | B1 | * | 9/2002 | Curro et al. ..................... 604/383 |
| 6,454,747 | B1 | * | 9/2002 | Shimada et al. ............... 604/312 |
| 6,478,785 | B1 | | 11/2002 | Ashton et al. |
| 6,511,465 | B1 | | 1/2003 | Freiburger et al. |
| 6,534,694 | B2 | * | 3/2003 | Kling et al. ..................... 604/366 |
| 6,645,190 | B1 | | 11/2003 | Olson et al. |
| 6,677,258 | B2 | * | 1/2004 | Carroll et al. .................. 442/394 |
| 6,843,872 | B2 | * | 1/2005 | Morman ......................... 156/163 |
| 6,939,906 | B2 | | 9/2005 | Hoshi et al. |
| 6,982,231 | B1 | * | 1/2006 | Uitenbroek et al. ........... 442/394 |
| 7,087,289 | B2 | * | 8/2006 | Soon et al. ..................... 428/137 |
| 2001/0008676 | A1 | | 7/2001 | Pelkie et al. |
| 2002/0104608 | A1 | | 8/2002 | Welch et al. |
| 2004/0147890 | A1 | * | 7/2004 | Nakahata et al. ......... 604/385.01 |
| 2004/0209042 | A1 | * | 10/2004 | Peacock ........................ 428/136 |
| 2004/0236300 | A1 | | 11/2004 | Gibbs et al. |
| 2005/0148730 | A1 | | 7/2005 | Day et al. |
| 2005/0190326 | A1 | | 9/2005 | Jeon et al. |
| 2005/0233153 | A1 | | 10/2005 | Qin et al. |
| 2005/0239941 | A1 | | 10/2005 | Miyamoto |
| 2006/0019045 | A1 | | 1/2006 | Bourgeois |
| 2006/0036225 | A1 | * | 2/2006 | Middlesworth et al. ....... 604/378 |
| 2006/0100478 | A1 | | 5/2006 | Connors et al. |

FOREIGN PATENT DOCUMENTS

| | | | |
|---|---|---|---|
| EP | 0634453 | A3 | 1/1995 |
| EP | 650714 | A1 * | 5/1995 |
| EP | 0854174 | A1 | 7/1998 |
| EP | 1333043 | A1 | 8/2003 |
| FR | 2686887 | A3 | 8/1993 |
| GB | 2270915 | A | 3/1994 |
| JP | 56090849 | | 7/1981 |
| JP | 8060121 | | 3/1996 |
| WO | WO 9500586 | A1 | 1/1995 |
| WO | WO 9516425 | A2 | 5/1995 |
| WO | WO 9611236 | A1 | 4/1996 |
| WO | WO 0037009 | A2 | 6/2000 |
| WO | WO 0037009 | A3 | 6/2000 |
| WO | WO 0202321 | A1 | 1/2002 |
| WO | WO 0222733 | A2 | 3/2002 |
| WO | WO 0222733 | A3 | 3/2002 |
| WO | WO 2004052940 | A2 | 6/2004 |
| WO | WO 2004052940 | A3 | 6/2004 |

OTHER PUBLICATIONS

NRL Report 4364, "Manufacture of Super-Fine Organic Fibers" by Wente et al., May 25, 1954.

NRL Report 5265, "An Improved Device for the Formation of Super-Fine Thermoplastic Fibers" by Lawrence et al., Feb. 11, 1959.

INDA Standard Test Method IST 70.4 (99), "Standard Test Method for Water Vapor Transmission Rate Through Non Woven and Plastic Film Using a Guard Film and Vapor Pressure Sensor," Copyright 1995, 7 pages.

English Abstract of Japanese Patent No. 04270746, Sep. 28, 1992.

English Abstract of Japanese Patent No. 07070380, Mar. 14, 1995.

English Abstract of Japanese Patent No. 08324676, Dec. 10, 1996.

English Abstract of Japanese Patent No. 11106565, Apr. 20, 1999.

English Abstract of Japanese Patent No. 2000239527, Sep. 5, 2000.

Abstract of Japanese Patent No. 58029842, Feb. 22, 1983.

Search Report and Written Opinion for PCT/US2006/007219, Jun. 21, 2006.

\* cited by examiner

WAIST ELASTIC MEMBERS FOR USE IN ABSORBENT ARTICLES

BACKGROUND OF THE INVENTION

Absorbent articles such as diapers, training pants, incontinence garments, swim undergarments, and the like conventionally include a liquid permeable body-facing liner, a liquid impermeable outer cover, and an absorbent core. The absorbent core is typically located in between the outer cover and the liner for taking in and retaining liquids (e.g., urine) exuded by the wearer.

Some of these absorbent articles contain various elastic materials to permit some expansion of the article when necessary to provide a better fit on the wearer. The elastic members are also designed to contract when being worn in order to provide the article with form-fitting properties at least in some areas.

For instance, some disposable diapers made in the past have included elastic fastener tabs that are typically joined to the rear portion of the article and are configured to releasably attach to the front of the article. In other configurations, diapers have also been constructed containing an elastic waistband that partially encircles the waist of a user.

The amount of stretch and elasticity present in an absorbent article in the transverse direction can have a significant impact upon the perceived comfort and fit of the garment. In the past, however, elastic waistbands have been limited in their size and thus generally have only provided elasticity around the waist opening of the article.

Thus, a need currently exists for an elastic waist member that provides elasticity not only along the waist opening but also provides transverse stretch properties towards the crotch of the absorbent article. A need also exists for a relatively large waist elastic member that extends towards the crotch of the absorbent article without interfering with the ability of the article to absorb fluids.

SUMMARY OF THE INVENTION

In summary, the present disclosure relates to disposable absorbent articles having improved stretch and fit properties. More particularly, the present disclosure is directed to incorporating into an absorbent article a breathable elastic film positioned generally in the waist region of the article. The breathable elastic film extends in the longitudinal direction of the article to provide form fitting properties not only near the waist area but also towards the crotch region of the article. The elastic film is also breathable so that the film does not interfere with the fluid management properties of the absorbent article. The absorbent article may comprise, for instance, a diaper, training pants, incontinence garments, swim pants, adult incontinence products, and the like.

In one embodiment, for instance, the present disclosure is directed to an absorbent article comprising a chassis including an outer cover, a bodyside liner and an absorbent structure. The absorbent structure is positioned in between the outer cover and the bodyside liner. The chassis includes a front region, a crotch region and a back region. The front region and the back region define a waist opening therebetween. The waist opening defines a front waist edge and a back waist edge. The chassis has a length extending in the longitudinal direction from the front waist edge to the back waist edge. The chassis further comprises a waist region surrounding the waist opening.

In accordance with the present invention, the absorbent article may further contain one or more waist elastic members located along the waist region. The waist elastic member has a first edge located at the front or back waist edge and a second edge opposite the first edge. The waist elastic member has a length in the longitudinal direction that is at least 25%, such as at least 33% of the length of the chassis. In one embodiment, the waist elastic member is positioned in between the bodyside liner and the outer cover. The waist elastic member comprises an elastic film. The elastic film defines apertures sufficient to allow fluid transmission therethrough. A plurality of apertures may be located along the length of the waist elastic member including apertures proximal to the second edge.

In one embodiment, the waist elastic member may have an extension tension as defined below of from about 200 to about 1500 g/3 inch, such as from about 400 to about 600 g/3 inch at 50% elongation. The retraction tension of the waist elastic member may be from about 100 to about 1000 g/3 inch, such as from about 300 to about 400 g/3 inch at 50% elongation during a second cycle. The waist elastic member may also be capable of being stretched at least 100% in the transverse or cross direction and may have a machine direction or longitudinal tension of at least 1500 g at 10% elongation.

As mentioned above, the waist elastic member is also breathable. For instance, the waist elastic member may have a water vapor transmission rate of at least about 500 Mocon, such as at least about 1400 Mocon. In other embodiments, the water vapor transmission rate can be at least about 10,000 Mocon or even at least about 25,000 Mocon depending upon the desired result.

In certain aspects, the waist elastic member may be perforated according to a particular pattern or in particular areas in order to have the desired stretch properties in combination with the desired breathability. For instance, in one embodiment, the waist elastic member may include alternating first and second zones that each define a surface area and wherein a greater percentage of the surface area in the first zones is apertured in relation to the percent of surface area apertured in the second zones. For instance, in one embodiment, the first zones may be apertured while the second zones may not be apertured. Alternatively, the first zones may have a greater aperture density or may contain apertures having a greater diameter than those in the second zone.

Similarly, the waist elastic member may have a middle section positioned in between a first side section and a second side section. The side sections and the middle section may each define a surface area and wherein a greater percentage of the surface area in the middle section is apertured in relation to the percent of surface area apertured in the side sections. For example, the side sections may contain no apertures. Alternatively, the side sections may have a lesser aperture density or may have apertures having a smaller diameter than those in the middle section. In this manner, breathability of the material is maximized in the areas of the elastic member most likely to come into contact with body liquids. The side sections, however, retain the desirable elastic properties.

The waist elastic member may have any suitable width in the lateral direction. For instance, the waist elastic member may form a band around the entire circumference of the waist region. Alternatively, the waist elastic member may only extend across a portion of the front region or only extend across a portion of the back region. In still other embodiments, multiple waist elastic members may be incorporated into the waist region of the article. For instance, the article may include a front waist elastic member and a back waist elastic member.

The waist elastic member may be made from any suitable elastomeric film material. For instance, the waist elastic member may be made from a material comprising a block copolymer or a metallocene catalyzed polymer. The waist elastic material may also comprise a laminate of film layers or a laminate of film and nonwoven layers.

The elastic film may be formed according to any suitable process. The apertures may also be formed according to any suitable process, such as by being vacuum formed or mechanically formed. When mechanically formed, for instance, the apertures may be formed using needle punching.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
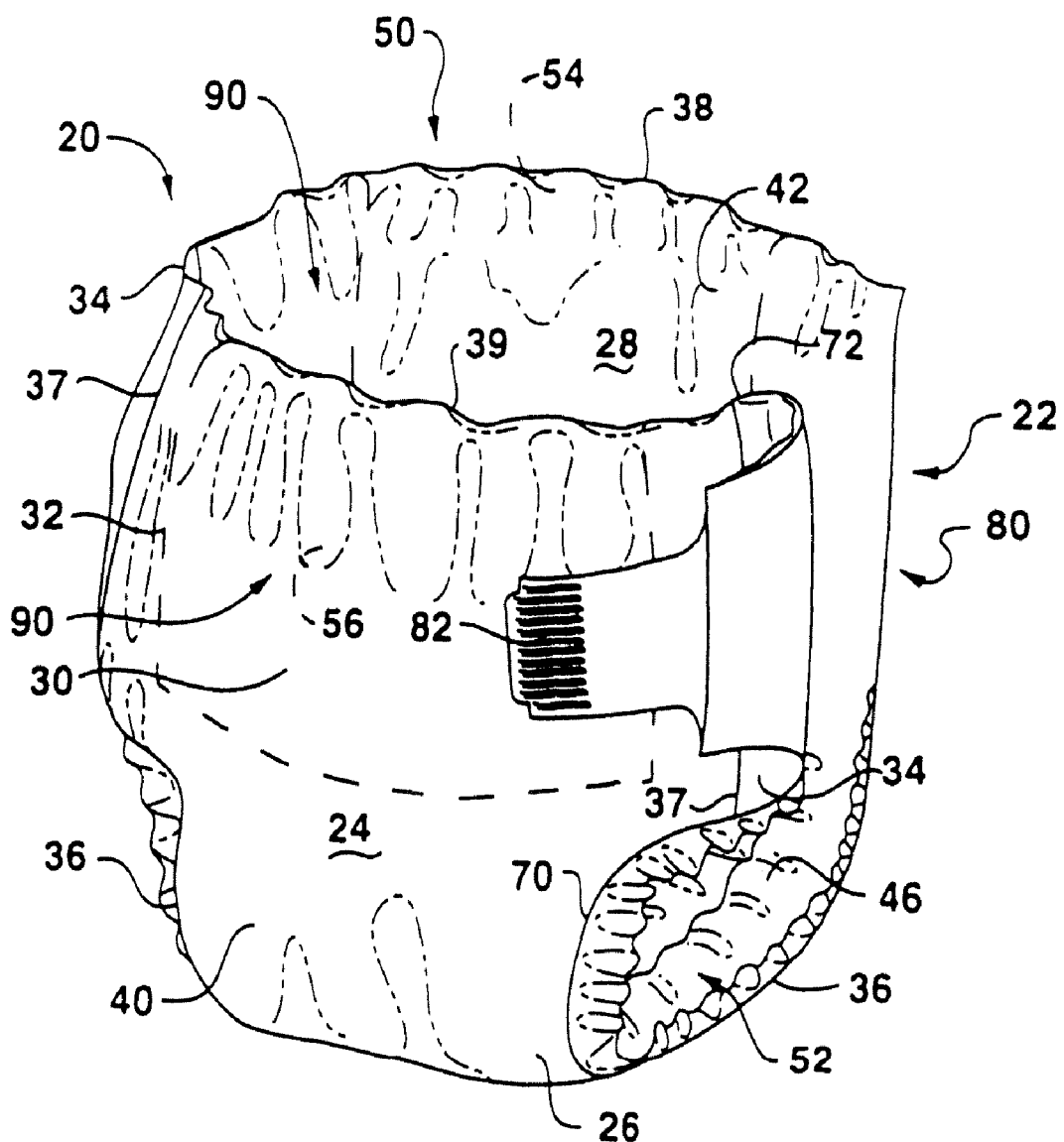
FIG. 1 is a rear perspective view of one embodiment of an absorbent article made in accordance with the present invention.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

In general, the present invention is directed to absorbent articles, such as diapers, that contain a waist elastic member that is breathable and has carefully controlled stretch properties. In particular, the products include a chassis having a front region and a back region that define a waist opening therebetween. The articles further include a crotch region positioned between the front and back region in the longitudinal direction and between a pair of leg openings in the lateral direction. Additionally, the chassis defines a waist region surrounding the waist opening.

For many applications, the chassis includes an absorbent structure positioned in between a bodyside liner and an outer cover. The bodyside liner is liquid permeable, while the outer cover is liquid impermeable. The absorbent structure is configured to hold and retain any body fluids that may come in contact with the bodyside liner.

In accordance with the present invention, a waist elastic member is placed in the waist region of the chassis between the bodyside liner and the absorbent structure. The waist elastic member has a length in the longitudinal direction that is at least 25%, such as at least 33%, such as at least 40% of the length of the chassis in the longitudinal direction. By providing a waist elastic member having a relatively long length, the waist elastic member serves to improve the fit of the article. Of particular advantage, the waist elastic member is made breathable so as to provide improved fit without an accumulation of body fluid in between the waist elastic member and the wearer.

For example, in order to make the waist elastic member breathable, in one embodiment, the waist elastic member defines various apertures that are placed at specific locations. The apertures may be formed into the waist elastic member, for example, by perforating the waist elastic member. The apertures are formed into the waist elastic member in a manner that not only makes the waist elastic member breathable, but that also preserves the elastic properties of the material. For instance, the apertures may be applied to the waist elastic member in a uniform manner over the entire surface area of the member or may only be located at specific areas on the waist elastic member. The diameter of the apertures and the aperture density may also be varied in order to ensure that the stretch properties of the waist elastic member fall within predefined limits.

For example, in one embodiment, the waist elastic member may have an extension tension of from about 200 to about 1500 g/3 inch at 50% elongation, such as from about 400 to about 600 g/3 inch at 50% elongation. The retraction tension of the waist elastic member may be from about 100 g/3 inch to about 1000 g/3 inch at 50% elongation during a second cycle, such as from about 300 g/3 inch to about 400 g/3 inch at 50% elongation during a second cycle. In one embodiment, the waist elastic member may also display at least a 100% cross direction or lateral stretch and may have a longitudinal or machine direction tension of at least about 1500 g at 10% elongation.

As used herein, the terms "elastic" or "elastomeric" are used interchangeably and refer to a property of a material where upon removal of an elongating force, the material is capable of recovering to substantially its unstretched size and shape or the material exhibits a significant retractive force. In particular, elastic materials utilized in connection with the present invention may be elongated/extended or stretched in at least one direction without breaking by at least 15%, such as by at least 25% (to at least 125% of its initial unstretched length) in at least one direction, suitably by at least 50% (to at least 150% of its initial unstretched length) and which will recover, upon release of the applied stretching or biasing force, at least 10% of their elongation. It is generally advantageous that the elastomeric material or composite be capable of being elongated by at least 100%, more desirably at least 200%, of its relaxed length and recover at least 30% and more desirably 50% of its elongation upon release of a stretching, biasing force, within about one minute.

Figure 2:
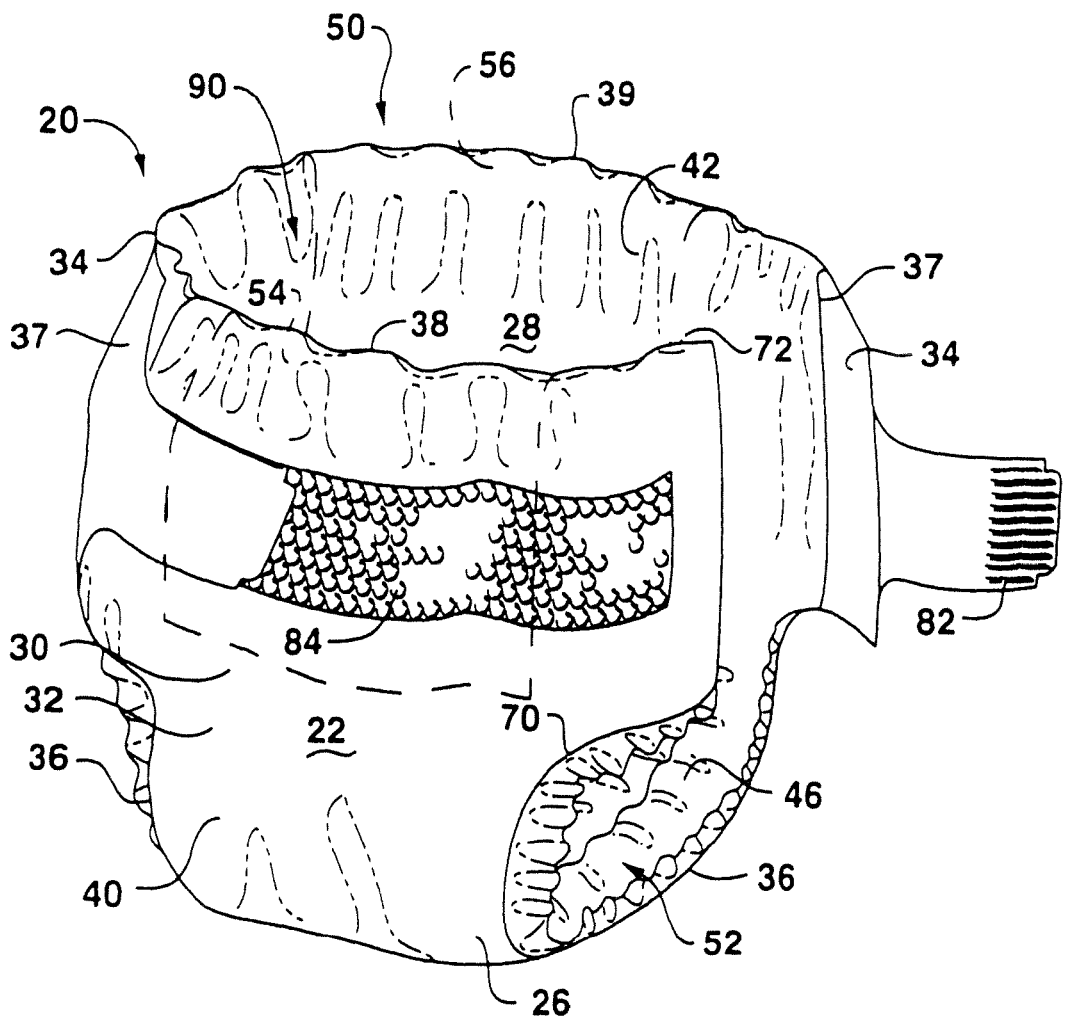
FIG. 2 is a front perspective view of the absorbent article illustrated in FIG. 1.

Referring to FIGS. 1 and 2, for exemplary purposes, an absorbent article 20 that may be made in accordance with the present invention is shown. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present invention.

By way of illustration only, various materials and methods for constructing absorbent articles such as the diaper 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
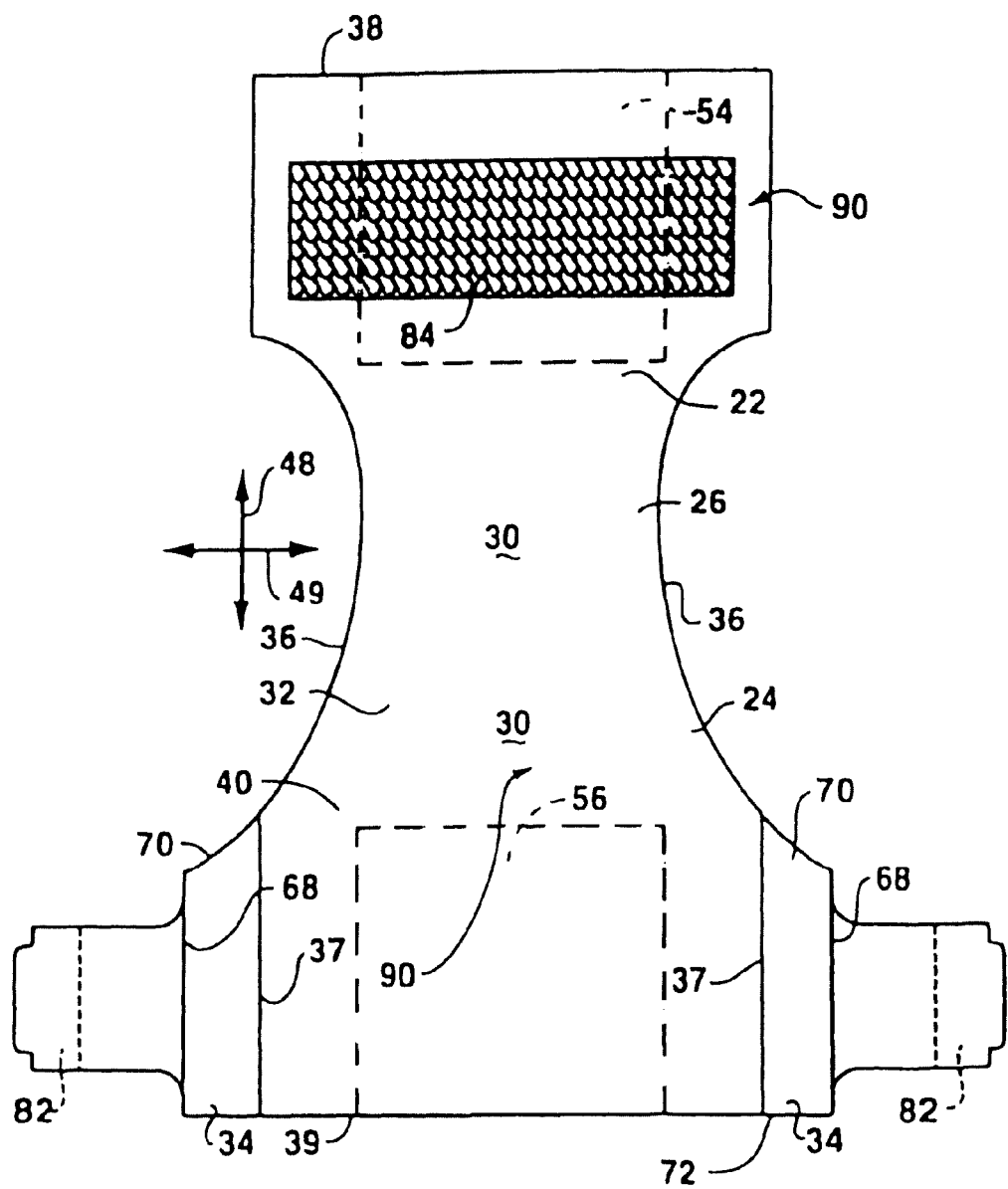
FIG. 3 is a plan view of the absorbent article shown in FIG. 1 with the article in an unfastened, unfolded and laid flat condition showing the surface of the article that faces away from the wearer.
Figure 4:
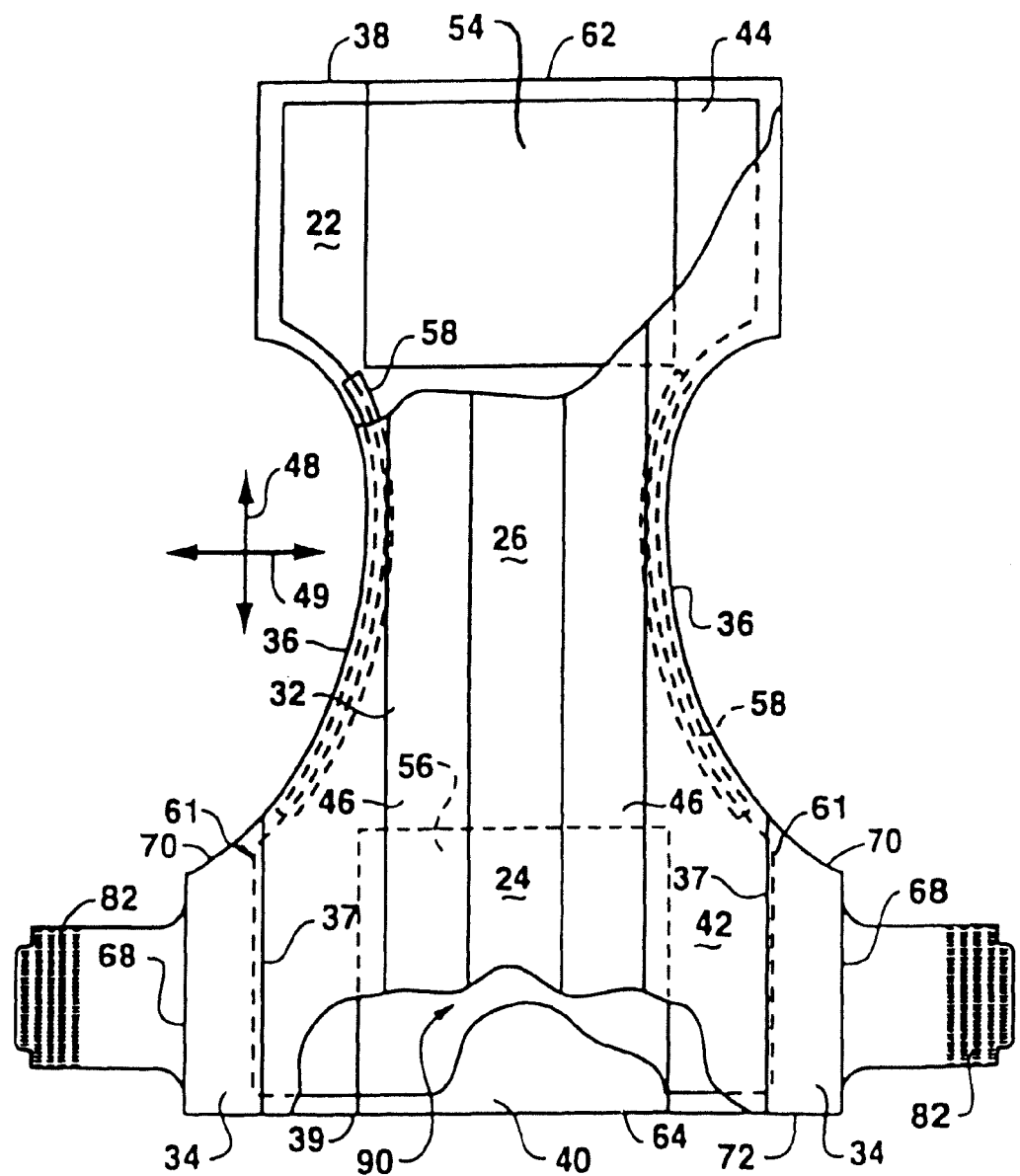
FIG. 4 is a plan view similar to FIG. 3 showing the surface of the absorbent article that faces the wearer when worn and with portions cut away to show underlying features.

A diaper 20 is representatively illustrated in FIG. 1 in a partially fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article when worn to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32, that, in this embodiment, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the diaper 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In some embodiments, the absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 32 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end.

The elastic side panels 34 each have a longitudinal outer edge 68, a leg end edge 70 disposed toward the longitudinal center of the diaper 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. As shown in FIG. 4, the outer edges 68 are generally parallel to the longitudinal direction 48 while the waist end edges 72 are generally parallel to the transverse axis 49. It should be understood, however, that in other embodiments the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the embodiment shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in the figures, the fastening components 82 are attached to the side panels 34 along the edges 68. In this embodiment, the fastening components 82 are not elastic or extendable. In other embodiments, however, the fastening components may be integral with the side panels 34. For example, the fastening components may be directly attached to the side panels 34 on a surface thereof.

As described above, the present disclosure is particularly directed to absorbent articles having improved stretch properties, especially within the front region and/or in the back region of the article. In this regard, as shown in FIGS. 1-4, the absorbent article 20 may include a breathable, waist elastic member 54 positioned in the front region 22 of the article and/or a breathable, waist elastic member 56 positioned in the back region 24 of the article 20. In the embodiment shown in FIG. 1, the absorbent article 20 includes the front waist elastic member 54 and the back waist elastic member 56. It should be understood, however, that multiple waist elastic members may be present in the front region and/or in the back region of the article. Further, in embodiments where the side panels of the chassis 32 are permanently bonded together, the waist elastic member 54 may extend around the entire circumference of the waist opening.

Of particular advantage, the waist elastic members 54 and 56 as shown in FIG. 1 extend a significant length in the longitudinal direction. For example, as shown, the waist elastic members 54 and 56 extend so as to cover a substantial portion of the front region 22 and the back region 24. For example, in one embodiment, the length of the waist elastic members 54 and 56 in the longitudinal direction are at least about 25%, such as at least about 33% of the entire length of the chassis in the longitudinal direction. For instance, in one particular embodiment, the waist elastic members 54 and 56 extend over at least about 40% of the length of the chassis 32.

Referring to FIG. 4, in one embodiment, the waist elastic members 54 and 56 are positioned in between the absorbent structure 44 and the bodyside liner 42. In order to prevent the waist elastic members 54 and 56 from interfering with the fluid control properties of the article, the waist elastic members in accordance with the present invention are breathable. In this manner, the waist elastic members 54 and 56 provide improved fit in the front region 22 and/or in the back region 24 of the absorbent article 20 without body fluid accumulation occurring in between the waist elastic member and the wearer.

In general, the waist elastic member comprises an elastic film that defines apertures in amounts sufficient to make the film breathable. The film may be used alone or may be incorporated into a laminate. The laminate, for instance, may comprise multiple layers of films or may comprise a film in combination with a fabric layer, such as a nonwoven layer.

The apertures formed into the film can have any suitable diameter and can be present on the film at any desired density in order for the film to have the desired characteristics. In one embodiment, for instance, the apertures have a diameter of from about 25 microns to about 2 mm, such as from about 50 microns to about 1 mm.

Similarly, the thickness of the film or film laminate may vary depending upon the desired properties. In general, the thickness of the film can be from about ½ mils to about 4 mils, such as from about 1 mil to about 3 mils.

The elastic film may be made from any suitable elastomeric material that possesses the desired stretch characteristics when apertured. Elastomeric materials may include cast or blown films comprised of polyolefin elastomers, such as a polyethylene elastomer or a polypropylene elastomer. For instance, in one embodiment, a metallocene catalyzed polyolefin elastomer may be used. Elastomeric polypropylene copolymers may also be used. The polypropylene elastomer, for instance, may comprise a copolymer with various rubber modifiers. Alternatively, the polypropylene elastomer may comprise a polyalphaolefin elastomer.

In an alternative embodiment or in combination with the above polymers, the elastic film may comprise a block copolymer. Suitable block copolymers include, for instance, styrene-isoprene-styrene (SIS) block copolymers, styrene-butadiene-styrene (SBS) block copolymers, styrene-ethylene butylene-styrene (SEBS) block copolymers and the like. Such block copolymers are commercially available under the name KRATON from Kraton Polymers of Houston, Tex.

The apertures may be created in the film as the film is being formed or may be created in the film in a post processing operation. For example, in one embodiment, the film is cast on a roll and then vacuum perforated while the film is still in a molten state. In an alternative embodiment, the apertures are formed into the film by needling the film after the film is formed. It should be understood, however, that the apertures may be formed into the film using any suitable process and the manner in which the apertures are formed is generally not critical to the present invention.

In many applications, the apertures formed into the film may serve to decrease the elastic properties of the film. Thus, in accordance with the present invention, a balance is desired between placing a sufficient amount of apertures in the film in order for the film to obtain a desired breathability level, while still maintaining the film within the desired elastic properties. This balance can be achieved by controlling location of the apertures, controlling the diameter of the apertures, controlling the density of the apertures, by selecting an appropriate thickness of the film, by selecting an appropriate film material, and the like.

For many applications, especially when incorporated into an absorbent article as shown in FIG. 1, the waist elastic member should have a breathability such that the waist elastic member has a moisture vapor transmission rate of at least about 500 Mocon, such as at least about 1400 Mocon, such as at least 10,000 Mocon, and, in one embodiment, can have a moisture transmission rate of at least 25,000 Mocon.

At the above moisture vapor transmission rates, the waist elastic member should also have an extension tension of at least about 200 g/3 inch to about 1500 g/3 inch at 50% elongation and should have a retraction tension of from about 100 g/3 inch to about 1000 g/3 inch at 50% elongation during a second cycle. The waist elastic member may also have at least 100% cross direction or transverse stretch and should have a minimum machine direction or longitudinal tension of at least about 1500 g at 10% elongation.

In order to provide sufficient breathability while controlling the elastic properties, in one embodiment, a greater percentage of the surface area of a middle portion of the waist elastic member is apertured in relation to two opposing side regions. In this manner, the middle area provides for the needed breathability, while the side regions provide the needed elastic properties.

Figure 5:
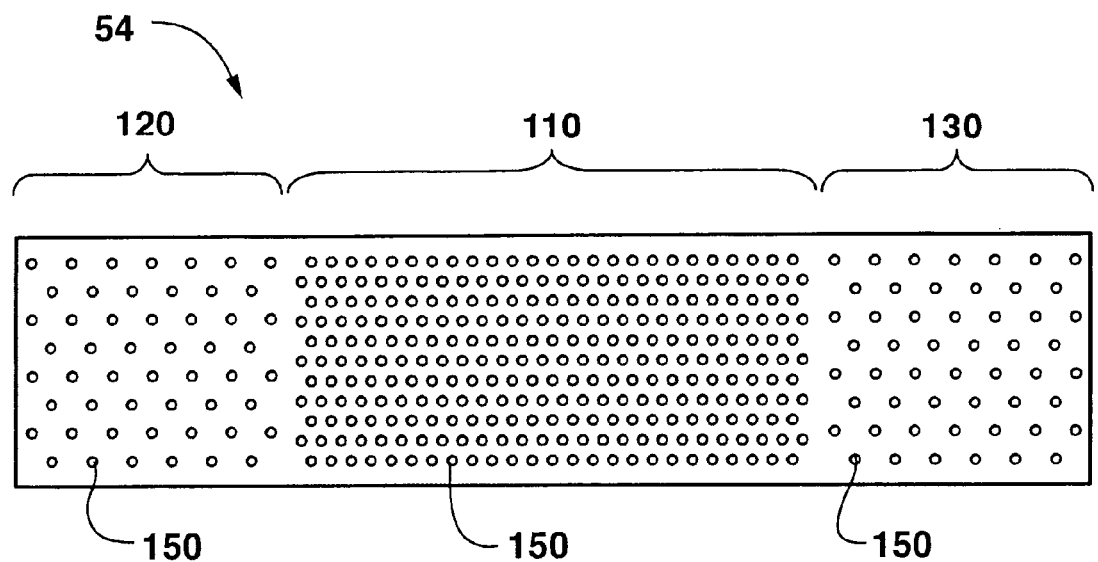
FIG. 5 is a plan view of one embodiment of a waist elastic member that may be used in the absorbent article illustrated in FIG. 1.

For example, referring to FIG. 5, one embodiment of a waist elastic member 54 made in accordance with the present invention is shown. As illustrated, the waist elastic member 54 includes a middle zone 110 separated by a pair of opposing side zones 120 and 130. The waist elastic member 54 further includes a plurality of apertures 150. In this embodiment, the density of apertures 150 is greater in the middle zone 110 as opposed to the density of apertures appearing in the side zones 120 and 130.

In the embodiment shown in FIG. 5, the width of the middle zone 110 is approximately equal to the width of the first side zone 120 and the second side zone 130 combined. It should be understood, however, depending upon the particular application, the size of the middle zone 110 in relation to the size of the side zones 120 and 130 may be altered. For instance, in an alternative embodiment, each of the zones may have an equal width.

Figure 6:
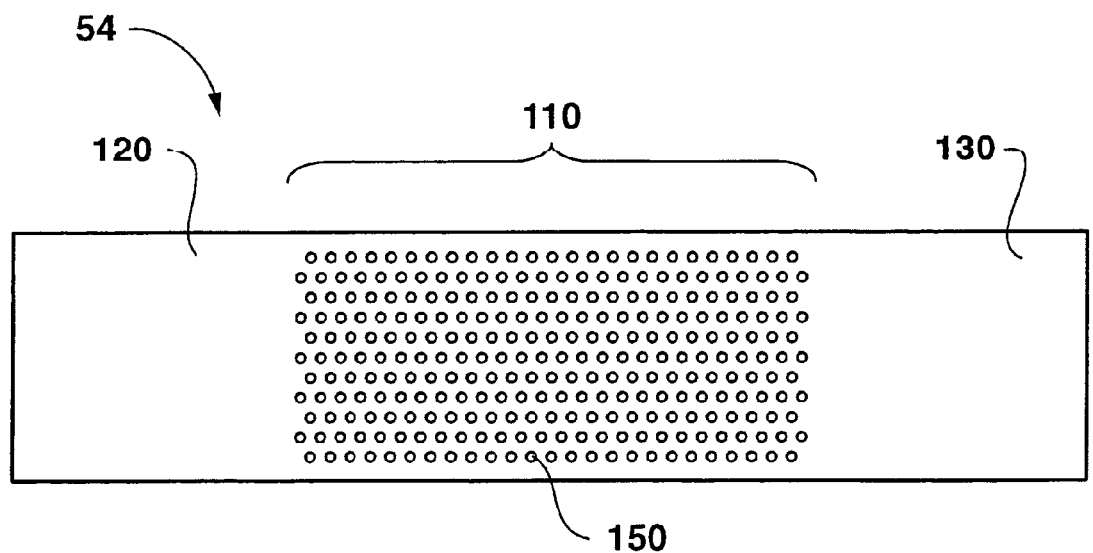
FIG. 6 is a plan view of another embodiment of a waist elastic member that may be incorporated into the absorbent article shown in FIG. 1.

Referring to FIG. 6, another embodiment of a waist elastic member 54 made in accordance with the present invention is shown. In this embodiment, the middle zone 110 includes apertures in a relatively high density. The side zones 120 and 130, however, do not contain any apertures. By not containing any apertures, the side zones 120 and 130 have high elasticity and resist tearing. The middle zone 110, however, is breathable, especially at the location most likely to come into contact with body fluids.

Figure 7:
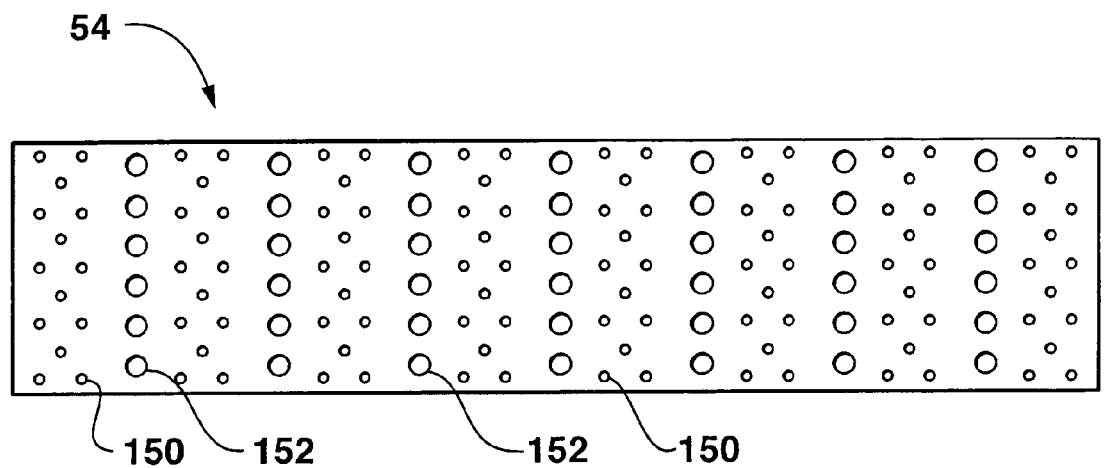
FIG. 7 is still another embodiment of a waist elastic member that may be incorporated into the absorbent article illustrated in FIG. 1.

Referring to FIG. 7, still another alternative embodiment of an waist elastic member 54 made in accordance with the present invention is shown. In this embodiment, the waist elastic member 54 is separated into alternating columns. The first columns contain relatively small apertures 150 while the second columns contain relatively large apertures 152. In this manner, the waist elastic member has alternating zones of breathability, intake and stretch.

Figure 8:
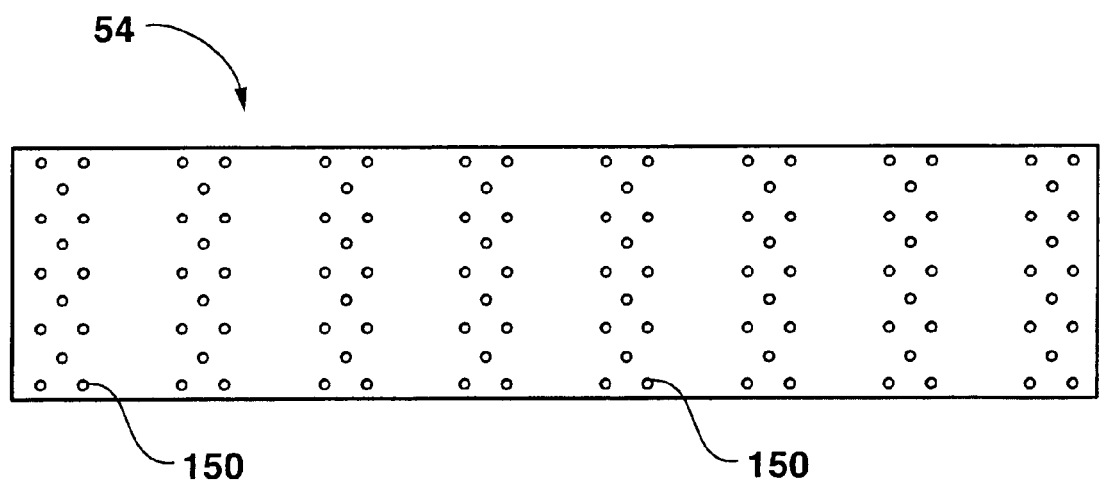
FIG. 8 is another embodiment of a waist elastic member that may be incorporated into the absorbent article shown in FIG. 1.

Referring to FIG. 8, still another embodiment of a waist elastic member 54 made in accordance with the present invention is shown. Similar to the embodiment shown in FIG. 7, the waist elastic member 54 includes alternating zones or columns of breathability and stretch. The first zones or columns contain apertures 150, while the second zones or columns are not apertured. The pattern of apertures as shown in FIG. 8 may be varied and controlled in order to control breathability and elasticity.

The remaining materials used to form the absorbent article 20 that surround the waist elastic members 54 and 56 may vary depending upon the particular application and the particular product being produced.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394, and Favor 9543 superabsorbents are available from DeGussa Superabsorbers.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference to the extent they are consistent (i.e., not in conflict) herewith.

Testing Procedures

Water Vapor Transmission Rate (WVTR)/Breathability:

A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. This information is used to calculate the transmission rate at which moisture is transmitted through the test material according to the equation:

$$TR^{-1}_{test\,material} = TR^{-1}_{test\,material,\,guardfilm,\,airgap} - TR^{-1}_{guardfilm,\,airgap}$$

Calculations:

WVTR: The calculation of the WVTR uses the formula:

$$WVTR = F p_{sat}(T) RH / (A P_{sat}(T)(1-RH))$$

where:
F=The flow of water vapor in cc/min.,
$p_{sat}(T)$=The density of water in saturated air at temperature T,
RH=The relative humidity at specified locations in the cell,
A=The cross sectional area of the cell, and,
$P_{sat}(T)$=The saturation vapor pressure of water vapor at temperature T.

For the purposes of this Application, the testing temperature for the above test was at about 37.8° C., the flow was at 100 cc/min, and the relative humidity was at 60%. Additionally, the value for n was equal to 6 and the number of cycles was 3.

Cycle Testing:

The materials were tested using a cyclical testing procedure to determine extension tension (load up), retraction tension (load down) and percent set. In particular, 2 cycle testing was utilized to 100 percent defined elongation. For this test, the sample size was 3 inch in the MD by 6 inch in the CD. The Grip size was 3 inch width. The grip separation was 4 inch. The samples were loaded such that the cross-direction of the sample was in the vertical direction. A preload of approximately 10-15 grams was set. The test pulled the sample at 20 inches/min (500 mm/min) to 100 percent elongation (2.8 inches in addition to the 4 inch gap), and then immediately (without pause) returned to the zero point (the 4 inch gauge separation). The results of the test data are all from the first and second cycles. The testing was done on a Sintech Corp. constant rate of extension tester 2/S with a Renew MTS mongoose box (controller) using TESTWORKS 4.07b software (Sintech Corp, of Cary, N.C.). The tests were conducted under ambient conditions.

Example

The following example was completed in order to demonstrate some of the materials that may be used to form waist elastic members in accordance with the present invention.

The following film materials were produced and tested for elastic properties. As shown below, one of the samples contained a single film layer, while the remaining samples contained multiple film layers.

TABLE 1

| Sample # | Outside Layers | Center Layer | Ratio of layers % in terms of thickness | Process | Aperture | Breathable |
|---|---|---|---|---|---|---|
| 1 | Chevron 1019 Polyethylene | Vector 4111 SIS Polymer from Dexco Blended with Vector 8508 SBS Polymer from Dexco | 5.75/88.5/5.75 | Blown-split bubble | No | No |
| 2 | Chevron 1019 Polyethylene | Vector 4111 SIS Polymer from Dexco Blended with Vector 8508 SBS Polymer from Dexco | 5.75/88.5/5.75 | Blown-split bubble | Yes | Yes |
| 3 | Chevron 1019 Polyethylene | Vector 4111 SIS Polymer from Dexco Blended with Vector 8508 SBS Polymer from Dexco | 4/92/4 | Blown-split bubble | No | No |
| 4 | Inner Layer 10% 1730, 10% White 80% Chevron 1019 Polyethylene Outer Layer 10% 1657 90% Chevron 1019 Polyethylene | Vector 4111 SIS Polymer from Dexco Blended with Vector 8508 SBS Polymer from Dexco | 3.5/94/2.5 | Blown-split bubble | No | No |
| 5 | Chevron 1019 Polyethylene | Vector 4111 SIS Polymer from Dexco Blended with Vector 8508 SBS Polymer from Dexco | 1.5/97/1.5 | Blown-collapsed | No | No |
| 6 | None | Vector 4111 SIS Polymer from Dexco | N/A | Blown-split bubble | No | No |
| 7 | 50% Chevron 1019 Polyethylene | Vector 4111 SIS Polymer from Dexco | 3.5/93/3.5 | Cast | No | No |

The above samples were then placed in a tensile testing apparatus and the following results were obtained:

TABLE 2

| Sample # | Basis Weight (gsm) | Load up @ 30% 1st cyc (Grams) | Load up @ 50% 1st cyc (Grams) | Load dn @ 50% 1st cyc (Grams) | Load dn @ 50% 2nd cyc (Grams) | % Hysteresis Loss Cycle 1 | % Hysteresis Loss Cycle 2 | Immed % Set Cycle 2 |
|---|---|---|---|---|---|---|---|---|
| 1 | 44 | 584 | 658 | 235 | 220 | 60 | 48 | 24 |
| 2 | 35 | 360 | 426 | 139 | 129 | 59 | 41 | 28 |
| 3 | 40 | 511 | 586 | 237 | 222 | 56 | 43 | 21 |
| 4 | 40 | 385 | 459 | 228 | 215 | 47 | 37 | 17 |
| 5 | 60 | 393 | 491 | 301 | 289 | 36 | 26 | 11 |
| 6 | 42 | 260 | 334 | 180 | 173 | 42 | 30 | 15 |
| 7 | 45 | 423 | 622 | 238 | 228 | 54 | 32 | 16 |

As shown above, each of the sample multi-layer films that were formed have elastic properties well suited for use in the present invention. As also shown, when Sample 2 was apertured, some elastic properties were lost as can be seen relative to Sample 1. However, Sample 2 demonstrates that the multi-layer film may be apertured while yet retaining sufficient elastic properties for use in absorbent articles.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article comprising:
a chassis including an outer cover, a bodyside liner and an absorbent structure, the absorbent structure being positioned in between the outer cover and the bodyside liner, the chassis including a front region, a crotch region, and a back region, the front region and the back region defining a waist opening therebetween, the waist opening defining a front waist edge and a back waist edge, the chassis having a length extending in the longitudinal direction from the front waist edge to the back waist edge, the chassis further comprising a waist region surrounding the waist opening; and
a waist elastic member located along the waist region with a first edge located at the front or back waist edge and a second edge longitudinally opposite the first edge, the waist elastic member positioned between the outer cover and the bodyside liner, the waist elastic member having a length in the longitudinal direction that is at least 25% of the length of the chassis, the waist elastic member comprising an elastic film, the elastic film defining apertures sufficient to allow fluid transmission therethrough wherein a plurality of apertures are located along the length of the waist elastic member including apertures proximal to the second edge.

2. The absorbent article as defined in claim 1, wherein the waist elastic member has an extension tension of from about 200 to about 1500 g/3 inch at 50% elongation and has a retraction tension of from about 100 to about 1000 g/3 inch at 50% elongation during a second cycle.

3. The absorbent article as defined in claim 1, wherein the waist elastic member has an extension tension of from about 400 to about 600 g/3 inch at 50% elongation and has a retraction tension of from about 300 to about 400 g/3 inch at 50% elongation during a second cycle and has a longitudinal tension of at least 1500 g at 10% elongation.

4. The absorbent article as defined in claim 1, wherein the waist elastic member has a moisture vapor transmission rate of at least 500 Mocon.

5. The absorbent article as defined in claim 1, wherein the waist elastic member has a moisture vapor transmission rate of at least 10,000 Mocon.

6. The absorbent article as defined in claim 1, wherein the waist elastic member has a middle section positioned in between a first side section and a second side section, and wherein the apertures are only located in the middle section.

7. The absorbent article as defined in claim 1, wherein the waist elastic member includes alternating first and second zones along the width of the waist elastic member, the first and second zones having a surface area and wherein a greater percentage of the surface area of the first zone is apertured in relation to the percent of surface area apertured in the second zone.

8. The absorbent article as defined in claim 1, wherein the waist elastic member includes a middle section positioned in between a first side section and a second side section, the side sections and the middle section each containing apertures and defining a surface area, and wherein a greater percentage of the surface area in the middle section is apertured in relation to the percent of surface area apertured in the side sections.

9. The absorbent article as defined in claim 8, wherein the middle section has a greater aperture density than the first and second side sections.

10. The absorbent article as defined in claim 8, wherein the apertures contained in the middle section have a greater diameter than the apertures contained in the first and second side sections.

11. The absorbent article as defined in claim 1, wherein the waist elastic member has a length in the longitudinal direction that is at least 33% of the length of the chassis.

12. The absorbent article as defined in claim 1, wherein the waist elastic member is made from a material comprising an elastomeric block copolymer or an elastomeric metallocene catalyzed polymer.

13. The absorbent article as defined in claim 1, wherein the waist elastic member comprises a band that extends all the way around the waist opening.

14. The absorbent article as defined in claim 1, wherein the waist elastic member only extends across at least a portion of the front region of the chassis or the back region of the chassis.

15. An absorbent article comprising:
a chassis including an outer cover, a bodyside liner and an absorbent structure, the absorbent structure being positioned in between the outer cover and the bodyside liner, the chassis including a front region, a crotch region, and a back region, the front region and the back region defining a waist opening therebetween, the waist opening defining a front waist edge and a back waist edge, the chassis having a length extending in the longitudinal direction from the front waist edge to the back waist edge, the chassis further comprising a waist region surrounding the waist opening; and a waist elastic member located along the waist region with a first edge located at the front or back waist edge and a second edge longitudinally opposite the first edge, the waist elastic member positioned between the outer cover and the bodyside liner, the waist elastic member having a length in the longitudinal direction that is at least 25% of the length of the chassis, the waist elastic member comprising an elastic film defining apertures wherein a plurality of apertures are located along the length of the waist elastic member including apertures proximal to the second edge, the apertures having a diameter of from about 25 microns to about 2 mm, the waist elastic member being breathable and having a moisture vapor transmission rate of at least about 1400 Mocon, the waist elastic member having an extension tension of from about 200 to about 1500 g/3 inch at 50% elongation and having a retraction tension of from about 100 to about 1000 g/3 inch at 50% elongation after a second cycle.

16. The absorbent article as defined in claim 15, wherein the waist elastic member includes alternating first and second zones along the width of the waist elastic member, the first and second zones having a surface area and wherein a greater percentage of the surface area of the first zone is apertured in relation to the percent of surface area apertured in the second zone.

17. The absorbent article as defined in claim 15, wherein the waist elastic member includes a middle section positioned in between a first side section and a second side section, the side sections and the middle sections each containing apertures and defining a surface area, and wherein a greater percentage of the surface area in the middle section is apertured in relation to the percent of surface area apertured in the side sections.

18. The absorbent article as defined in claim 17, wherein the middle section has a greater aperture density than the first and second side sections.

19. The absorbent article as defined in claim 17, wherein the apertures contained in the middle section have a greater diameter than the apertures contained in the first and second side sections.

20. The absorbent article as defined in claim 15, wherein the waist elastic member has a length in the longitudinal direction that is at least 33% of the length of the chassis.

* * * * *